United States Patent [19]

Ikenaka et al.

[11] Patent Number: 5,319,078

[45] Date of Patent: Jun. 7, 1994

[54] α-AMYLASE ASSAY USING MODIFIED OLIGOSACCHARIDE AND PROCESS FOR PRODUCING SAID MODIFIED OLIGOSACCHARIDE

[75] Inventors: Tokuji Ikenaka, Sakai; Kaoru Omichi, Toyonaka; Shinji Satomura, Osaka; Yuko Nagamine, Toyonaka, all of Japan

[73] Assignee: Wako Pure Chemical Industries, Inc., Osaka, Japan

[21] Appl. No.: 972,801

[22] Filed: Nov. 6, 1992

Related U.S. Application Data

[60] Division of Ser. No. 465,660, Dec. 29, 1989, Pat. No. 5,192,666, which is a continuation of Ser. No. 72,208, Oct. 10, 1987, abandoned.

[30] Foreign Application Priority Data

| Jul. 11, 1986 [JP] | Japan | 61-163054 |
| Jan. 9, 1987 [JP] | Japan | 62-2730 |
| Jan. 26, 1987 [JP] | Japan | 62-15776 |

[51] Int. Cl.$^5$ .................... C12Q 1/40; C07H 5/04; C07H 15/00
[52] U.S. Cl. ................... 536/18.7; 536/17.1; 435/22
[58] Field of Search ............ 536/17.1, 18.7; 435/22

[56] References Cited

U.S. PATENT DOCUMENTS

| 4,000,042 | 12/1976 | Adams | 195/103 |
| 4,169,765 | 10/1979 | Keyes | 435/22 |
| 4,622,295 | 11/1986 | Ikenaka . | |
| 4,649,103 | 3/1987 | Blair . | |
| 4,681,841 | 7/1987 | Matsumoto . | |
| 5,192,666 | 3/1993 | Ikenaka et al. | 435/22 |

FOREIGN PATENT DOCUMENTS

| 0171960 | 2/1986 | European Pat. Off. . |
| 0173255 | 3/1986 | European Pat. Off. . |
| 3000292 | 7/1981 | Fed. Rep. of Germany . |
| 60-237998 | 11/1985 | Japan . |

OTHER PUBLICATIONS

Omichi et al. *J. Biochem.*, 93, 1055 (1983).
Omichi et al., *J. Biochem.*, 99, 1245 (1986).
Methods in Carbohydrate Chemistry, vol. 2, p. 236 (1963).

*Primary Examiner*—Ronald W. Griffin
*Attorney, Agent, or Firm*—Armstrong, Westerman, Hattori, McLeland & Naughton

[57] ABSTRACT

α-Amylase activity can be determined rapidly and precisely by using as a substrate a modified oligo-saccharide wherein a benzylozymethyl group or a halo-methyl group is bonded to the $C_6$ position of non-reducing-end glucose residue and the reducing-end glucose residue is bonded to a group which exhibits an optically measurable change upon cleavage. Processes for producing such a compound are also disclosed.

4 Claims, 7 Drawing Sheets

α-AMYLASE ASSAY USING MODIFIED OLIGOSACCHARIDE AND PROCESS FOR PRODUCING SAID MODIFIED OLIGOSACCHARIDE

This application is a divisional application of Ser. No. 07/465,660 filed Dec. 29, 1989, now U.S. Pat. No. 5,192,666 which was a continuation of Ser. No. 07/072,208, filed Oct. 10, 1987, now abandoned.

BACKGROUND OF THE INVENTION

This invention relates to a process for determining the activity of α-amylase in a sample using a modified oligosaccharide as a substrate and a process for producing such a modified oligosaccharide.

Heretofore, various processes for determining the activity of o-amylase using a modified oligosaccharide as a substrate have been proposed. For example, U.S. Pat. No. 4,649,108 to Blair discloses a method of measuring the amount of α-amylase in liquid sample comprising the steps of providing an oligosaccharide substrate for α-amylase, said substrate containing at least 3 glucose units, the reducing-end glucose residue (unit) being bonded, via a bond cleavable by α- or α-glucosidase, to a label which exhibits an optically measurable change upon cleavage of said bond, and the non-reducing-end (terminal) glucose residue being bonded to a blocking group which inhibits cleavage by exo-enzymes of the bond between said non-reducing-end glucose residue and the adjacent glucose residue; contacting said sample with said oligosaccharide substrate and with a first added exo-enzyme capable of cleaving the bond between said reducing-end glucose residue and said label, and a second added exo-enzyme capable of cleaving bonds between glucose units, to form a mixture comprising said substrate, said first exo-enzyme, and said second exo-enzyme; and measuring said optically measurable change. According to said U.S. patent, the blocking groups can be carboxylic acid esters, phosphate esters, sulfonate esters, ethers (such as benzyl, silyl, and triphenylmethyl), monosaccharides other than α-1,4 linked glucose, and acetal or ketal blocking groups such as benzylidene (column 4 lines 37–67). But the ester blocking groups are unstable since they are easily hydrolyzed in an aqueous solution. Further, when the size of the blocking group becomes larger as in the case of toluenesulfonyl, methanesulfonyl, silyl or triphenylmethyl, the solubility in water is undesirably lowered. In addition, the introduction of a blocking group into the non-reducing-end glucose residue has many problems, and the ester and ether groups as mentioned above cannot be introduced into the non-reducing-end glucose residue by the process disclosed at from column 4 line 63 to column 7 line 58 of said U.S. patent. Therefore, according to said U.S. patent, preferably the substrate has eight or fewer glucose units, and most preferably has six or seven, and preferred blocking substituents are acetals or ketals, e.g. benzylidene (column 2 lines 4–7).

When the most preferred oligosaccharide according to said U.S. patent, that is, an oligosaccharide having 6 or 7 glucose units and benzylidene as the blocking group, is used as a substrate for measuring α-amylase, there are many problems in that the hydrolysis rate by α-amylase is slow, various kinds of hydrolyzed products are produced due to many positions to be hydrolyzed, the reaction for liberating the color producing group becomes many and complicated due to many hydrolyzed products, the amount of coupling enzymes to be used becomes larger, and thus the reliability for the measurement becomes insufficient. The improvement of these disadvantages has long been desired.

SUMMARY OF THE INVENTION

This invention provides a process for determining the activity of α-amylase in a sample which comprises using as a substrate for α-amylase a modified oligosaccharide of the formula:

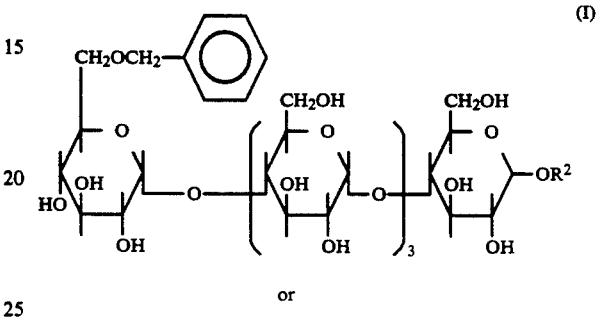

or

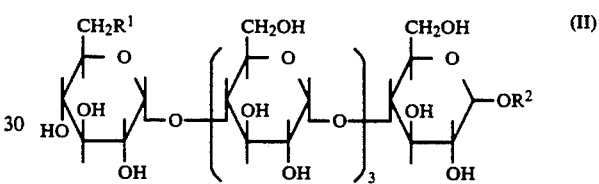

wherein $R^1$ is a halogen atom; and $R^2$ is a group of the formula:

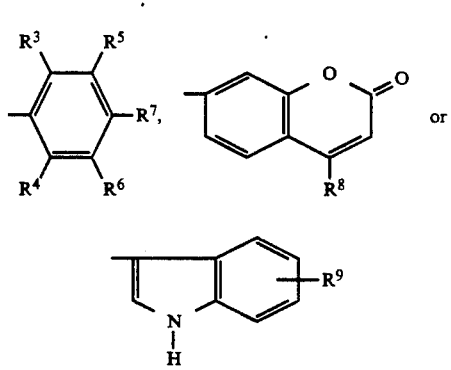

in which $R^3$ through $R^6$ are independently hydrogen, a lower alkyl group, a lower alkoxy group, a nitro group, a carboxyl group, a sulfonic acid group or a halogen atom, and $R^3$ and $R^5$, and/or $R^4$ and $R^6$, may be bonded to form an aromatic ring; $R^7$ is hydrogen, a lower alkoxy group, a halogen atom, or a nitro group; $R^8$ is hydrogen, a methyl group, or a trifluoromethyl group; and $R^9$ is hydrogen or a halogen atom, contacting said sample with said substrate in the presence of at least one exo-enzyme, and measuring an optically measurable change as a measure of α-amylase activity in said sample.

This invention also provides a process for producing an oligosaccharide having a special substituent at the non-reducing-end glucose residue such as that represented by the formula (I) or (II), which comprises reacting a modified cyclodextrin with cyclomaltodextringluconotransferase in the present of an acceptor, and then reacting with glucoamylase or α-glucosidase.

This invention further provides a process for producing an oligosaccharide having a special substituent at the non-reducing-end glucose residue such as that represented by the formula (I), which comprises reacting an oligosaccharide having a substituent which exhibits an optically measurable change upon cleavage at the reducing-end glucose residue with an aldehyde, a ketone, an acetal or a ketal to form 4,6-O-cyclic acetal or 4,6O-cyclic katal at the non-reducing-end glucose residue, and reducing said 4,6O-cyclic acetal or ketal.

DESCRIPTION OF THE PREFERRED EMBODIMENTS

Figure 1:
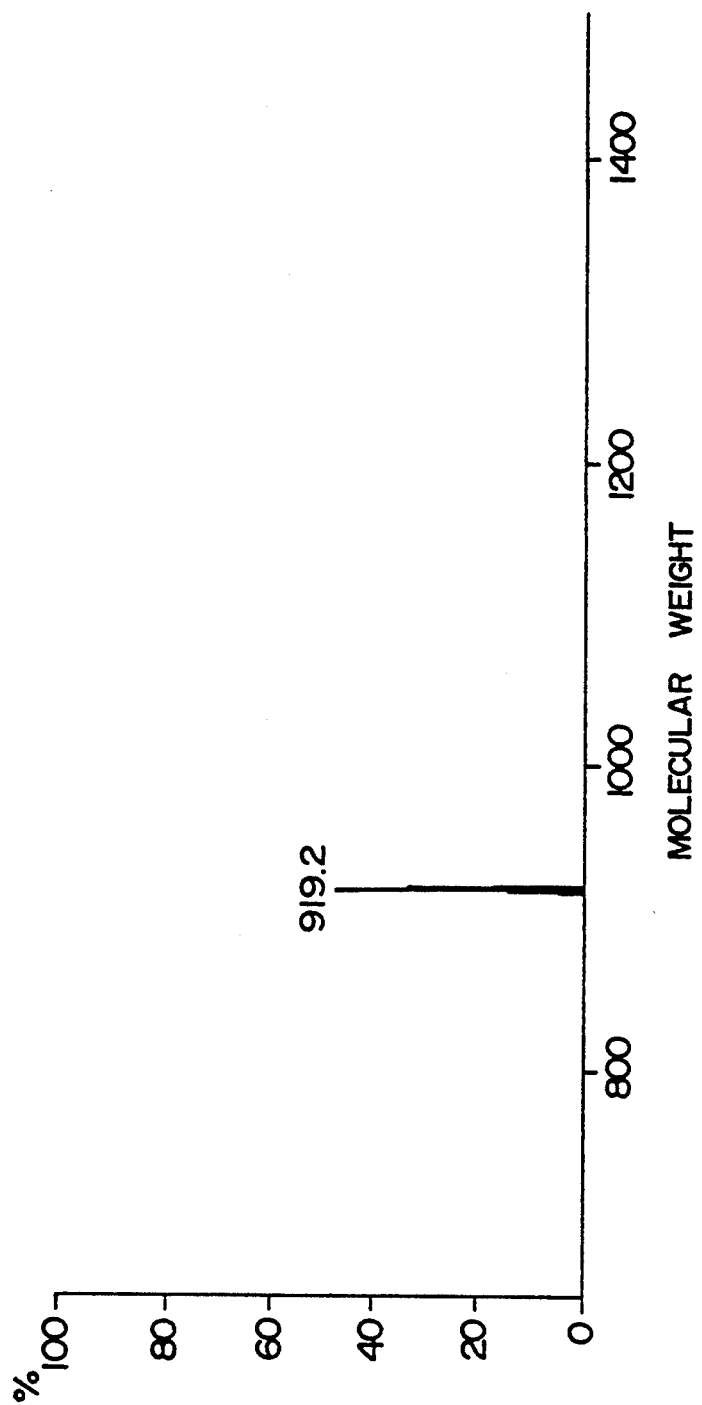
FIGS. 1 and 2 are FAB mass spectra of the oligosaccharides obtained in Examples 3 and 5 (apparatus: Jeol HX-100), respectively.

The modified oligosaccharide used as a substrate for α-amylase is represented by the formula:

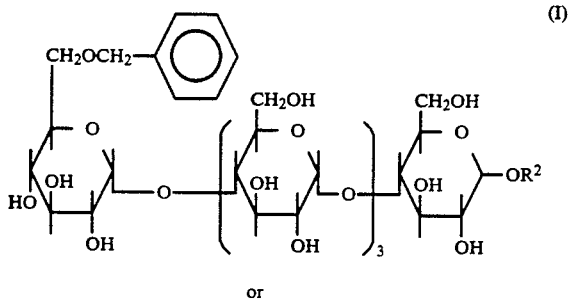

(I)

or

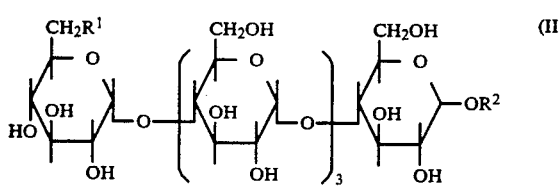

(II)

wherein $R^1$ is a halogen atom such as bromine, chlorine, iodine, etc.; and $R^2$ is a group of the formula:

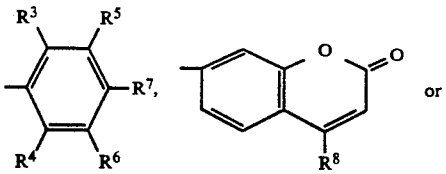

or

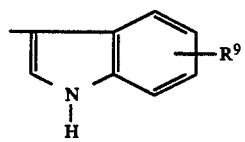

in which $R^3$ through $R^6$ are independently hydrogen, a lower alkyl group preferably having 1 to 4 carbon atoms, a lower alkoxy group preferably having 1 to 4 carbon atoms, a nitro group, a carboxyl group, a sulfonic acid group, or a halogen atom such as chlorine, bromine, iodine, etc., and $R^3$ and $R^5$, and/or $R^4$ and $R^6$, may be bonded to form an aromatic ring; $R^7$ is hydrogen, a lower alkoxy group preferably having 1 to 4 carbon atoms, a halogen atom such as chlorine, bromine, iodine, etc., or a nitro group; $R^8$ is hydrogen, a methyl group, or a tri-fluoromethyl group; and $R^9$ is hydrogen or a halogen atom such as chlorine, bromine, iodine, etc.

The oligosaccharides of the formula (I) and (II) have advantages in that the hydrolysis rate is fast, that is, the sensitivity as a substrate is high, the Michaelis constant ($K_m$) which is defined as a substrate concentration for giving a half of the maximum rate ($V_{max}$) of α-amylase is small, that is the specificity as a substrate is high and the required substrate concentration for measuring activities of α-amylase is low (usually used in the concentration of the value of $K_m \times 5$ to 10), and the position of hydrolysis is almost one position, that is, the color production reaction from the hydrolyzed products can be carried out simply and easily.

The above-mentioned advantages can be shown by using the following oligosaccharides:

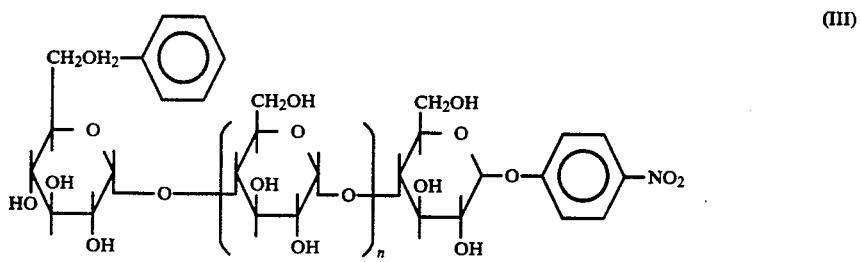

(III)

n = 2: BG4P
n = 3: BG5P (the present invention)
n = 4: BG6P
n = 5: BG7P

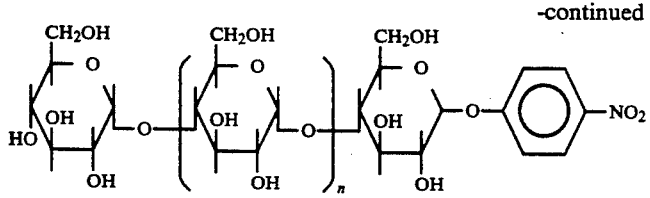

n = 2: G4P
n = 3: G5P (standard)
n = 4: G6P
n = 5: G7P

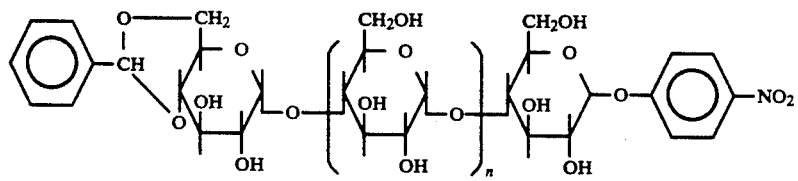

n = 2: BDG4P
n = 3: BDG5P
n = 4: BDG6P
n = 5: BDG7P

The hydrolysis rate is measured by using human pancreatic α-amylase (HPA) or human salivary α-amylase (HSA) for each substrate (1.0 mM) at pH 7, and evaluating by means of relative values by taking the value of G5P as 1.

The results are shown in Table 1.

TABLE 1

| Substrate | α-amylase | |
|---|---|---|
| | HPA | HSA |
| G4P | 0.70 | 0.75 |
| G5P | 1.0 | 1.0 |
| G6P | 1.7 | 1.7 |
| G7P | 1.8 | 1.8 |
| BG4P | 0.55 | 0.60 |
| BG5P | 1.4 | 1.4 |
| BG6P | 1.4 | 1.4 |
| BG7P | 1.5 | 1.5 |
| BDG4P | 0 | 0 |
| BDG5P | 0 | 0 |
| BDG6P | 0.4 | 0.5 |
| BDG7P | 1.1 | 1.0 |

The $K_m$ values were calculated by least square method according to a Lineweaver-Burle plot. The amounts of the products were measured with HPLC.

A mixture of 20 μl of α-amylase solution and 200 μl of 1.2 mM substrate solution in 50 mM BES [N,N-bis(2-hydroxyethyl)-2-aminoethanesulfonic acid]/NaOH buffer (pH 7.6), containing 20 mM sodium chloride and 2 mM calcium chloride was incubated at 37° C. for 5 min. Then 25 μl of the reaction mixture was added to 500 μl of 5% acetic acid to stop the reaction. The sample (100 μl) was analyzed by HPLC to examine the amounts of the products.

The results are shown in Table 2.

TABLE 2

| Substrate | $K_m$ value | |
|---|---|---|
| | HPA | HSA |
| G5P | 0.36 mM | 0.31 mM |
| | 0.34 g/l | 0.29 g/l |
| BG5P | 0.11 mM | 0.10 mM |
| | 0.11 g/l | 0.10 g/l |
| BDG7P | 0.086 mM | 0.10 mM |

TABLE 2-continued

| Substrate | $K_m$ value | |
|---|---|---|
| | HPA | HSA |
| | 0.12 g/l | 0.14 g/l |

The binding mode of each substrate were measured with high-performance liquid chromatography (HPLC) as described above.

The results are shown in Table 3.

TABLE 3

| | α-amylase | | | | | | | (%) |
|---|---|---|---|---|---|---|---|---|
| | HPA | | | | HSA | | | |
| | Hydrolysis product | | | | | | | |
| Substrate | G4P | G3P | G2P | GP | G4P | G3P | G2P | GP |
| G4P | 0 | 0 | 55 | 45 | 0 | 0 | 74 | 26 |
| G5P | 0 | 12 | 73 | 15 | 0 | 11 | 83 | 6 |
| G6P | 0 | 76 | 22 | 2 | 0 | 53 | 40 | 7 |
| G7P | 55 | 30 | 14 | 1 | 60 | 30 | 8 | 2 |
| BG4P | 0 | 0 | 8 | 92 | 0 | 0 | 10 | 90 |
| BG5P | 0 | 0 | 95 | 5 | 0 | 0 | 98 | 2 |
| BG6P | 0 | 73 | 23 | 4 | 0 | 68 | 29 | 3 |
| BG7P | 40 | 38 | 20 | 2 | 45 | 38 | 15 | 2 |
| BDG4P | Not hydrolyzed | | | | Not hydrolyzed | | | |
| BDG5P | | | | | | | | |
| BDG6P | 0 | 12 | 73 | 15 | 0 | 10 | 66 | 24 |
| BDG7P | 13 | 22 | 48 | 7 | 15 | 25 | 55 | 5 |

As is clear from the results of Tables 1 to 3, only BG5P satisfies the three requirements, that is, the high hydrolysis rate, low $K_m$ value and almost one position at the hydrolysis in which G2P is produced mainly. Since G3P or G4P is not produced by the hydrolysis, it is possible to measure α-amylase activity by using as exoenzyme only α-glucosidase which sufficiently hydrolyzes G2P but does not hydrolyze G3P or G4P sufficiently.

The activity of α-amylase can be measured by using the modified oligosaccharide of the formula (I) or (II) as follows:

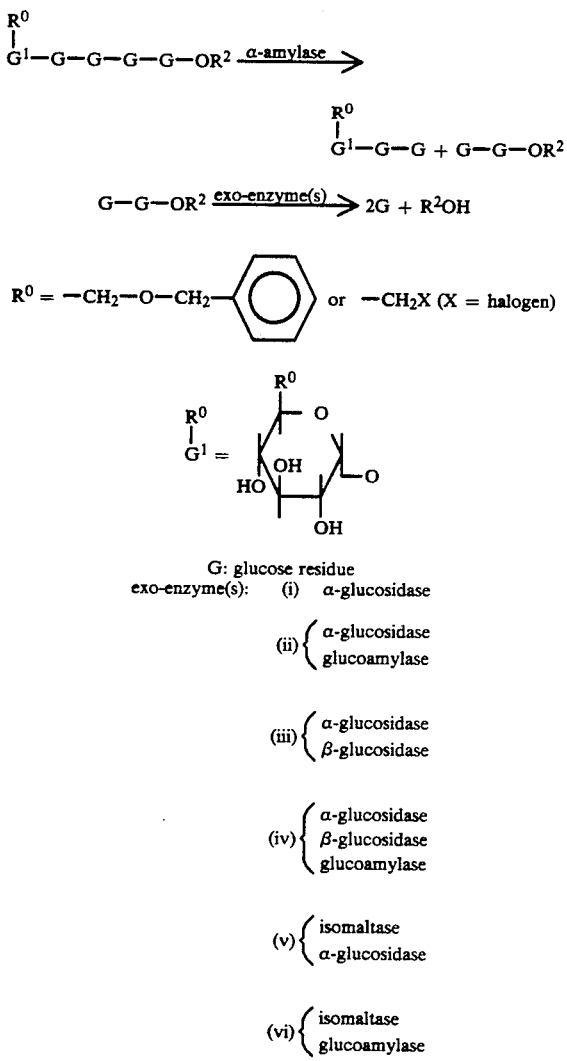

G: glucose residue
exo-enzyme(s): (i) α-glucosidase (ii) { α-glucosidase
      glucoamylase (iii) { α-glucosidase
       β-glucosidase (iv) { α-glucosidase
      β-glucosidase
      glucoamylase (v) { isomaltase
     α-glucosidase (vi) { isomaltase
      glucoamylase The substituent $R^0$ is attached to the $C_6$ position of the non-reducing-end glucose residue and the substituent $OR^2$ is attached to the $C_1$ position of the reducing end glucose residue and represented by, for example, a phenoxy group which may have one or more substituent groups, a naphthoxy group which may have one or more substituent groups, an umbelliferyl group which may have one or more substituent groups, or an indoxyl group which may have one or more substituent groups.

That is the α-amylase in a sample first acts on the modified oligosaccharide of the formula (I) or (II) to produce

wherein the primary alcohol group (—CH$_2$OH) at the $C_6$ position of the non-reducing end glucose residue is replaced by the substituent $R^0$, and G-G-OR$^2$ wherein OR$^2$ is as defined above. Then, G-G-OR$^2$ is reacted with coupling enzyme(s) such as glucoamylase, α-glucosidase, β-glucosidase and the like to produce 2G and R$^2$-OH which exhibits an optically measurable change. When R$^2$-OH is a nitrophenol such as p-nitrophenol, the activity of α-amylase in a sample can be obtained by directly measuring the absorption spectrum thereof (e.g. absorbance at 405 nm). When R$^2$-OH is phenol or naphthol having no nitro group (or capable of having a nitro group) such as phenol, o-chlorophenol, 2,6-dichlorophenol, p-methoxyphenol, or the like, it is reacted with a coupler such as 4-aminoantipyrine, or 3-methyl-2-benzothiazolinone hydrazone (MBTH) in the presence of an oxidase such as catechol oxidase, laccase, tyrosinase or monophenol oxidase, or an oxidant such as iodic acid or periodic acid; or peroxidase and hydrogen peroxide to produce a dye, the absorption spectrum of which is measured. When R$^2$-OH is a compound emitting fluorescence such as umbelliferone or 4-methylumbelliferone, the fluorescence intensity is measured. Further, when 2-OH is indoxyl, the absorption spectrum of indigo dyes produced by oxidation is measured.

The concentration of the modified oligosaccharide used as a substrate in the determination of the activity of α-amylase is not particularly limited but usually is about 0.1 to 10 mM.

As a sample to be measured, any ones containing α-amylase can be used. For example, there can be used as living body fluids blood, serum, urine, saliva, and the like.

As the exo-enzyme which is a coupling enzyme, there can be used α-glucosidase, a mixture of α-glucosidase and glucoamylase, a mixture of α-glucosidase and β-glucosidase, a mixture of α-glucosidase, β-glucosidase and glucoamylase, a mixture of α-glucosidase and isomaltase, and a mixture of isomaltase and glucoamylase. These exo-enzymes may be derived from animals, plants and microorganisms. The amount of exo-enzymes used is usually 0.5 to 100 units/ml, preferably 2 to 50 units/ml.

The reaction temperature is not particularly limited and preferably about 25° C. to 40° C. The reaction time can be selected properly depending on the purposes.

The pH of the reaction is not particularly limited and preferably about 6 to 8. As a buffer for maintain the pH proper, there can be used a phosphate buffer, a tris(hydroxymethyl)aminomethane-HCl buffer, a Good's buffer, and the like.

As an activation imparting agent for α-amylase, there can be used sodium chloride, calcium chloride, potassium chloride, calcium acetate and the like.

As the coupler for coupling (oxidation condensation) the phenol or naphthol liberated by the action of the exo-enzyme(s), there can be used 4-aminoantipyrine, 3-methyl-2-benzothiazolinonehydrazone (MBTH), p-amino-N,N-diethylaniline, and the like.

As the oxidase for coupling (oxidation condensation) of the phenol or naphthol with the coupler, there can be used laccase, catechol oxidase, tyrosinase, monophenol oxidase, and the like, derived from animals, plants, and microorganisms, in an amount of usually 0.2 to 10 units/ml, preferably 0.5 to 4 units/ml.

As the oxidizing agent for coupling (oxidation condensation), there can be used iodic acid and/or a salt thereof such as sodium, potassium, and the like salt, periodic acid and/or a salt thereof such as sodium, potassium salt, hydrogen peroxide, and the like.

Since the primary alcohol (—CH$_2$OH) at the $C_6$ position of the non-reducing-end glucose residue of the modified oligosaccharide of the formula (I) or (II) is replaced by the

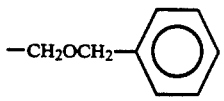

or —CH$_2$X (X=halogen), the modified oligosaccharide of the formula (I) or (II) cannot be used as a substrate for glucoamylase, α-glucosidase, β-glucosidase or isomaltase as it is. But since the modified oligosaccharide of the formula (I) or (II) is easily soluble in water and excellent in affinity for α-amylase, it can be a good specific substrate for α-amylase. Thus, the α-amylase determination process using as a substrate the modified oligosaccharide of the formula (I) or (II) does not bring about side reactions and has a very small blank value. Further the reagent solution for the measurement is very stable. In addition, since human α-amylase is almost hydrolyzed one glycosidic linkage of the modified oligosaccharide of formula (I) or (II), the stoichiometry is established, which results in making the kinetic determination of α-amylase possible.

Moreover, in the process for determining the activity of α-amylase of this invention, since the main product produced by reacting with α-amylase is G2P, the duration of the lag period can be shortened by reacting with at least one coupling enzyme (exo-enzyme) such as glucoamylase, α-glucosidase, isomaltase or β-glucosidase in the reaction after the α-amylase reaction. Thus the determination of the α-amylase activity can be carried out with high sensitivity and good linearity.

In the process for determining the activity of α-amylase of this invention, the measurement of an optically measurable change can be carried out by measuring absorption spectra of nitrophenols or indigo dyes liberated, by measuring absorption spectra of dyes formed by oxidation coupling of phenols or naphthols liberated with 4-aminoantipyrine, MBTH, or the like, or by measuring fluorescence intensity of umbelliferone liberated, so that the determination process is hardly influenced by sugars such as glucose, maltose and the like, reducing substances such as ascorbic acid, bilirubin, and the like present in samples to be measured.

The α-amylase activity determination process of this invention can be applied to either a rate assay wherein the reaction rate under certain conditions is measured, or an end point assay wherein a reaction terminator is used.

Further, the α-amylase activity determination process of this invention can well be suited to an auto analyzer and if necessary can be applied to a manual method.

In addition, since a so-called colorimetric method wherein the color of a dye developed is measured can be used by the use of the modified oligosaccharide of the formula (I) or (II), the process of this invention can also be applied to a test paper method which is a very simple method and a so-called dry determination process wherein multi-layer analysis sheets containing reaction reagents (multi-layer one-body type quantitative analysis films) are used.

The modified oligosaccharides of the formula (I) and (II) can be produced by reacting a modified cyclodextrin with cyclomaltodextrin-glucanotransferase in the presence of an acceptor, and then reacting with glucoamylase or α-glucosidase.

Such a process can also be applied to the Production of a variety of compounds similar to the oligosaccharides of the formula (I) and (II).

These compounds can be represented by the formula:

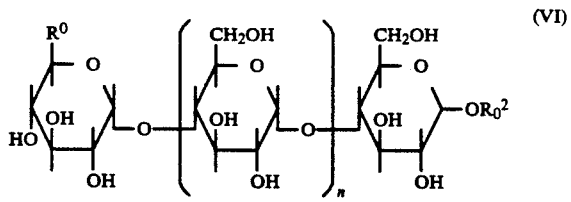

wherein $R^0$ is an alkoxymethyl group, a benzyloxymethyl group, an aminomethyl group, a carboxyl group or a halomethyl group; $R^2_o$ is the same group as defined in $R^2$ or a glucitol residue; and n is an integer of 2 to 5.

As the modified cyclodextrin, there can preferably be used those having one modified glucose residue per molecule, and may contain those having two or more modified glucose residues per molecule.

As the modified glucose residue, there can be used substituted glucose wherein the hydroxyl group in the glucose is replaced by a substituent which can emit fluorescence, e.g. a 2-pyridylamino group, 3-pyridylamino group, etc.; a substituent which can absorb UV light, e.g. an anilino group, a methylanilino group, a hydroxyanilino group, a carboxyphenylamino group, etc; an alkoxy group such as a methoxy group, an ethoxy group, etc.; a substituted alkoxy group such as a carboxymethoxy group, a hydroxyethoxy group, a benzyloxy group, a phenetyloxy group, a pyridylmethyloxy group, etc.; a halogen atom such as chlorine, bromine, etc.; a hydrazono group, a phenylhydrazono group or an amino group; or there can be used glucuronic acid wherein the —CH$_2$OH group at the C$_6$ position of glucose is replaced by a —COOH group.

As the acceptor, there can be used glucose, maltose, maltotriose, and derivatives thereof having as a substituent, e.g. p-nitrophenyl, phenyl, umbelliferyl, naphtyl, When maltotetraose or higher oligosaccharides are used, the reaction is slow and causes side reactions undesirably. On the other hand, when the glucose chain becomes longer, the glucose chain of major product in the initial reaction also becomes longer. Therefore, the glucose chain length of 1 to 3 is properly selected and used as the acceptor depending on the glucose chain length of the desired product. When a glucose derivative is used as the acceptor, the position of substituent is preferably the C$_1$ position, irrespective of α-substitution or β-substitution. Glucose derivatives having one or more substituents at C$_2$, C$_3$ and/or c$_6$ positions are not so preferable since the reaction is difficult to proceed. When the substituents at C$_2$, C$_3$ and/or C$_6$ positions are desired, it is preferable to use maltase wherein one or more substituents are introduced into C$_2$, C$_3$ and/or C$_6$ positions of the reducing end glucose residue.

As the substituent of the hydroxyl group at the C$_1$ position of the modified glucose-residue of the acceptor, there can be used the group represented by the formula: —OR$^2_O$ wherein R$^2_O$ is as defined above.

Concrete examples of the —OR$^2$ $_O$ groups are a P-nitrophenoxy group, a m-nitrophenoxy group, an o-chlorophenoxy group, a p-chlorophenoxy group, a 2,6-dichlorophenoxy group, an o-methoxyphenoxy group, a p-methoxyphenoxy group, an o-methylphenoxy group, an o-carboxyphenoxy group, an o-sulfophenoxy group, a 1-naphthoxy group, a 2-sulfo-1-naphthoxy group, a 2-carboxy-1-naphthoxy group, an umbelliferyl group, a 4-methylumbelliferyl group, an indoxyl group, glucitol residue, etc.

The cyclomaltodextrin-glucanotransferase (hereinafter referred to as "CGTase") is not particularly limited to its origin and source. There can be used those derived from Bacillus macerans, Bacillus megaterium, Klebsiella pneumonie, alcaligenous, etc.

The modified cyclodextrin can easily be obtained by using α-, β- or γ-cyclodextrin as a starting material and reacting with various reactants for introducing the desired modifying groups thereinto according to processes for producing various modified glucoses described in, for example, Method in Carbohydrate Chemistry I (1962) to V (1965), published by Academic Press. The selection of α-, β- or γ-cyclodextrin is optional and can be determined depending on the glucose chain length of the desired modified oligosaccharide derivative and its maximum yield.

The pH of the reaction of the modified cyclodextrin with CGTase in the presence of an acceptor changes slightly depending on the origin of CGTase, but usually 6 to 8. Any buffering agent which does not inhibit the enzymatic reaction can be used for maintaining the suitable pH. Examples of the buffering agents are Good's buffer, ammonium acetate buffer, carbonate buffer, phosphate buffer, etc.

The modified cyclodextrin is used in a concentration of preferably 1 to 50 mmol/l and the acceptor is used in a concentration of 1 mmol/l or more to the solubility limit.

The acceptor is preferably used in an amount of 5 moles or more per mole of the modified cyclodextrin.

The CGTase is preferably used in an amount of 50 to 5000 U/ml. The reaction is preferably carried out at 20° to 50° C. After the enzymatic reaction, CGTase is deactivated by heating, for example at 90° C. or higher for minutes or more, or by changing the pH, for example pH of 4.0 or less.

The reaction using glucoamylase or α-glucosidase can preferably be carried out at most suitable pH, for example pH 4 to 6, and using glucoamylase or α-glucosidase in an amount of preferably 5 to 100 U/ml.

Alternatively, the modified oligosaccharide of the formula (I) can be produced by reacting an oligosaccharide having a substituent which exhibits and optically measurable change upon cleavage at the reducing-end glucose residue with an aldehyde, a ketone, an acetal or a ketal to form 4,6-O-cyclic acetal or 4,6-O-cyclic ketal at the non-reducing end glucose residue, and reducing said 4,6-O-cyclic acetal or ketal.

Such a process can also be applied to the production of a variety of compounds similar to the oligosaccharide of the formula (I).

These compounds can be represented by the formula:

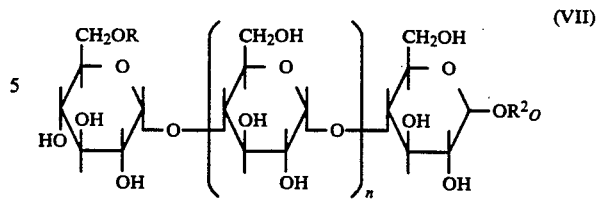

wherein R is a benzyl group, a substituted benzyl group (the substituent group is a lower alkyl group preferably having 1 to 4 carbon atoms, a lower alkoxy group preferably having 1 to 4 carbon atoms, an alkyl-substituted amino group, a carboxyl group, a nitro group, or a halogen atom such as chlorine, bromine, iodine, etc.), a 2-, 3- or 4-pyridylmethyl group, a straight- or branched-chain or cyclic alkyl group having 1 to 6 carbon atoms, or an alkenyl group having 1 to 6 carbon atoms; $R^2_O$ is the same group as defined in $R^2$ or a glucitol residue; and n is an integer of 2 to 5.

The oligosaccharide used as a starting material can be represented by the formula:

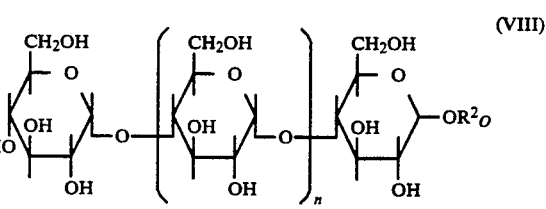

wherein $R^2_O$ and n are as defined above.

First, the oligosaccharide derivative of the formula (VIII) is reacted with an aldehyde, a ketone, an acetal or a ketal to form a cyclic acetal between the $C_4$ and $C_6$ positions of the non-reducing-end-glucose residue. The oligosaccharide derivative of the formula (VIII) is available commercially or can be synthesized by a process described in, for example, Japanese Patent Unexamined Publication No. 54-51892.

As the aldehyde, there can be used aromatic aldehyde such as benzaldehyde, tolylaldehyde, etc.; aliphatic aldehydes such as formaldehyde, acetaldehyde, propionaldehyde, butylaldehyde, etc.

As the ketone, there can be used acetone, methyl ethyl ketone, etc.

As the acetal, there can be used methylal, benzaldehyde dimethylacetal, acetaldehyde dimethylacetal, acetaldehyde diethylacetal, etc.

As the ketal, there can be used methyl ethyl ketone ethyleneketal, cyclohexanone dimethylketal, etc.

Further, there can also be used any aldehydes, ketones, acetals and ketals which can form a cyclic acetar or cyclic ketal,between the $C_4$ and $C_6$ positions of the non-reducing end glucose residue of the oligosaccharide derivative of the formula (VII).

The aldehyde, ketone, acetal or ketal is used in an amount of preferably 1 to 100 moles per mole of the oligosaccharide derivative (VIII).

The reaction is preferably carried out in the presence of a Lewis acid catalyst such as p-toluenesulfonic acid, zinc chloride, or the like, in a suitable solvent such as N,N-dimethylformamide (DMF), and the like. at from room temperature to a reflux temperature for 0.5 to 12 hours.

The resulting intermediate having the cyclic acetal is usually subjected to modification of other hydroxyl groups by acylation, followed by a reduction step.

The acylation can be carried out by a conventional process, for example, in the presence of a base such as pyridine and using as an acylating agent such as acetic anhydride, acetylchloride, benzbylchloride, etc.

The acylation step is not essential but is preferable to enhance the solubility in a reaction solvent used in the next step (the reduction step).

The reduction step is usually carried out by using a reducing agent in the presence of an acid catalyst such as aluminum chloride, boron trifluoride, zinc chloride, p-toluenesulfonic acid, methanesulfonic acid, hydrogen chloride gas (or blown into ether) etc., in a suitable solvent (e.g. tetrahydrofuran (THF), etc.) usually at 0°-50° C. for several tens minutes to several hours.

As the reducing agent, there can be used sodium cyanoborohydride, lithium aluminumhydride, pyridineborane, dimethylamineborane, trimethylamineborane, t-butylamineborane, diborane, etc. The reducing agent is preferably used in an amount of 1 to 1000 moles per mole of the oligosaccharide derivative (VIII).

The acid catalyst is preferably used in an amount of 0.5 to 5 moles per mole of the reducing agent.

When the acyl protection is conducted, deacylation is conducted by a conventional process, for example, by treating with a 0.01 to 1.0N sodium methoxidemethanol solution for several to several tens hours at from room temperature to slightly elevated temperatures to easily give the modified oligosaccharide of the formula (VII). Individual after-treatments after individual steps can be carried out by conventional processes. The final product can be purified by a conventional process such as column chromatography, and the like.

Since the α-1,4 bond of the oligosaccharide is subjected to acid hydrolysis under acidic conditions, or methanolysis under anhydrous methanol-HCl conditions, or the stability of glycosidic bond (the bonding between the reducing end glucose residue and the —OR² group) under acidic conditions is unknown, it was unknown whether the modified oligosaccharide of the formula (VII) derived from the oligosaccharide of the formula (VIII) could withstand under such a reducing treatment. But unexpectedly, the present inventors have found for the first time that ring-opening of the cyclic acetal portion was possible and accomplished the present invention.

In the formula (VII), the lower alkyl group in the substituted benzyl group includes a methyl group, an ethyl group, a propyl group, a butyl group, etc.; the lower alkoxy group in the substituted benzyl group includes a methoxy group, an ethoxy group, a propoxy group, a butoxy group, etc.; the alkyl-substituted amino group includes a dimethylamino group, a diethylamino group, an N-ethyl-N-(β-hydroxyethyl)amino group; the straight- or branched-chain or cyclic clkyl group having 1 to 6 carbon atoms includes a methyl group, an ethyl group, an iso-propyl group, a n-butyl group, a tert-butyl group, a n-pentyl group, an iso-amyl group, a n-hexyl group, a cyclopentyl group, a cyclohexyl group, etc.; the alkenyl group having 1 to 6 carbon atoms includes an ethenyl group, a 2-propenyl group, a 2-butenyl group, etc.

The group of the formula: —OR²$_O$ in the formula (VII) is bonded to the reducing end glucose residue and can be hydrolyzed by the action of glucoamylase-[E.C.3.2.1.3], α-glucosidase[E.C.3.2.1.20.], β-glucosidase [E.C.3.2.1.21.], isomaltase-[E.C 3.2.1.10] or β-amylase[E.C.3.2.1.2.], etc., to form nitrophenols which have absorptions by themselves at visible light range, to finally form dyes by coupling with couplers by the action of oxidases such as catechol oxidase, laccase, tyrosinase and monophenol oxidase, or to finally form dyes by coupling with couplers by the action of oxidants.

Examples of the group of the formula: —OR²$_O$ in the formula (VII) are a p-nitrophenoxy group, a m-nitrophenoxy group, an o-chlorophenoxy group, a p-chlorophenoxy group, a 2,6-dichlorophenoxy group, a 2-chloro-4-nitrophenoxy group, an o-methoxyphenoxy group, a p-methoxyphenoxy group, an o-methylphenoxy group, an carboxyphenoxy group, an o-sulfophenoxy group, a 1-naphthoxy group, a 2-sulfo-1-naphthoxy group, a 2-carboxy-1-naphthoxy group, etc.; an umbelliferyl group, a 4-methylumbelliferyl group, a 4-trifluoromethylumbelliferyl group, etc.; an indoxyl group, 5-bromoindoxyl group, 4-chloro-3-bromoindoxyl group, etc; a glucitol residue, etc.

The compounds of the formulae (VI) and (VII) can be used as substrates for determining the activity of α-amylase.

A part of the modified oligosaccharide of this inventions can effectively be used as a substrate for a fractional measuring method of α-amylase derived from the salivary glands and o-amylase derived from pancreas, that is, a fractional measuring method of α-amylase isozymes wherein decomposed products produced by hydrolysis of α-amylase are reacted with two or more coupling enzymes having different substrate specificities and the produced products are measured to conduct fractional measurements of α-amylase derived from human pancreas and α-amylase derived from human salivary glands.

This invention is illustrated by way of the following Examples.

EXAMPLE 1

Synthesis of p-nitrophenyl O-6-deoxy-6-[(2-pyridyl)-amino]-α-D-glucopyranosyl-(1→4)-O-α-D-glucopyranosyl-(1→4)-O-α-D-glucopyranosyl-(1→4)-O-α-D-glucopyranosyl-(1→4)-α-D-glucopyranoside (hereinafter referred to as "FG5P")

(1) Synthesis of mono-6-deoxy-6[(2-pyridyl)amino]-β-cyclodextrin (hereinafter referred to as "F-β-CD")

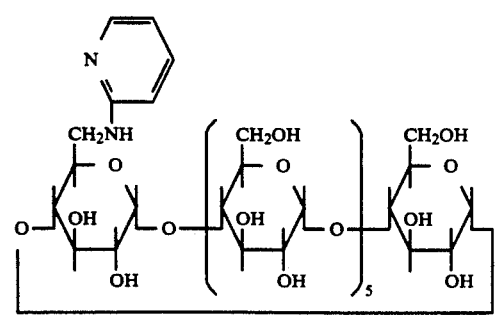

In 120 ml of dimethylsulfoxide (DMSO), 20 g of β-cyclodextrin and 30.4 g of dicyclohexylcarbodiimide (DCC) were dissolved and 2.6 ml of dichloroacetic acid was added thereto and stirred at room temperature for 30 minutes. To this, a solution obtained by dissolving 12.8 g of oxalic acid in 50 ml of methanol was added and the reaction solution was made pH 9 with 2M aqueous solution of sodium carbonate. Further, a solution obtained by dissolving 1.6 g of 2-aminopyridine in 200 ml of water was added thereto, followed by addition of 3.6 g of pyridine borane to carry out the reaction at 65°-70° C. for 2 hours. Then, 700 ml of water was added to the reaction solution and an insoluble matter was removed by filtration. Then, the reaction solution was made pH 7 with HCl, followed by addition of 2.4 g of sodium borohydride to carry out the reaction at room temperature for 1 hour. HCl was added to the reaction solution to make the pH 3 and to decompose excess sodium borohydride, followed by addition of ammonia water to make the pH 7.0. After adding 2 liters of acetone, a deposited precipitate was filtered to yield 3.0 g of F-$\beta$-CD.

Elementary analysis: $C_{47}H_{74}O_{34}N_2$

|  | C (%) | H (%) | N (%) | O (%) |
| --- | --- | --- | --- | --- |
| Calcd. | 46.61 | 6.16 | 2.31 | 44.92 |
| Found | 46.61 | 6.17 | 2.42 | 44.80 |

(2) Synthesis of FG5P

In 1 liter of 10 mM ammonium acetate buffer (pH 6.5), 10 g of F-$\beta$-CD and 10 g of p-nitrophenyl $\alpha$-glucoside were dissolved, and 1000 kU of CGTase was added thereto and reacted at 37° C. for 5 hours. The reaction solution was made pH 4.0 with acetic acid and 20 kU of glucoamylase (derived from Rhizopus niVeus) was added thereto and reacted at 37° C. for 10 hours. After freeze-drying the reaction solution, purification was carried out by using a column (30×1500 mm) packed with Bio-Gel p-2 (mfd. by Bio-Rad Co.) equilibrated with 50 mM acetic acid to give 1.1 g of FG5P.

The same reaction and aftertreatment as mentioned above were conducted by using 10 g of p-nitrophenyl $\beta$-glucoside in place of 10 g of p-nitrophenyl $\beta$-glucoside to give 2.5 g of $\beta$-form FG5P.

The structure was identified by the method disclosed in Japanese Patent Unexamined Publication No. 61-83195.

EXAMPLE 2

Synthesis of p-nitrophenyl
O-(6-O-carboxymethyl)-$\alpha$-D-glucopyranosyl-(1→4)
-O-$\alpha$-D-glucopyranosyl-(1→4)-O-$\alpha$-D-glucopyranosyl-(1→4)
-O-$\alpha$-D-glucopyranosyl-(1→4)-$\alpha$-D-glucopyranoside
(hereinafter referred to as "CMG5P")

(1) Synthesis of mono-O-carboxymethyl-$\beta$-cyclodextrin (hereinafter referred to as "CM-$\beta$-CD")

In 120 ml of water, 15.0 g of $\beta$-cyclodextrin and 13.5 g of sodium hydroxide were dissolved and 90 ml of a 10% monochloroacetic acid aqueous solution was added thereto and stirred at 25° C. for 5 hours. After making the reaction solution pH 7.0 with 6N HCl, 600 ml of acetone was added and deposited precipitate was filtered to give 12 g of CM-$\beta$-CD.

Elementary analysis: $C_{44}H_{75}O_{37}N$, MW 1210 ($NH_4$ salt)

|  | C (%) | H (%) | O (%) | N (%) |
| --- | --- | --- | --- | --- |
| Calcd. | 43.67 | 6.25 | 48.92 | 1.16 |
| Found | 43.66 | 6.28 | 48.86 | 1.20 |

(2) Synthesis of CMG5P

In 1 liter of 10 mM ammonium acetate buffer (pH 6.5), 10 g of CM-$\beta$-CD and 10 g of p-nitrophenylglucoside were dissolved, and 1000 kU of CGTase was added thereto and reacted at 37° C. for 5 hours. Then, the pH was made 4.0 with acetic acid, and 20 kU of glucoamylase was added thereto and reacted at 37° C. for 10 hours. After freeze-drying the reaction solution, purification was carried out by using a column (30×1500 mm) packed with Bio-Gel p-2 (mfd. by Bio-Rad Co.) equilibrated with 50 mM acetic acid to give 0.5 g of CMG5P together with 3 g of $C_2$ position substituted body and 1.7 g of $C_3$ position substituted body.

EXAMPLE 3

Synthesis of phenyl O-($\alpha$-D-glucopyranosyl uronicacid)
-(1→4)-O-$\alpha$-D-glucopyranosyl-(1→4)-O-$\alpha$-D-glucopyranosyl-(1→4)
-O-$\alpha$-D-glucopyranosyl-(1→4)-$\alpha$-D-glucopyranoside
(hereinafter referred to as "carboxyl G5P")

(1) Synthesis of monocarboxyl-$\beta$-cyclodextrin (hereinafter referred to as carboxyl-$\beta$-CD)

In 1 liter of water, 50 g of $\beta$-cyclodextrin was dissolved, and 5 g of platina-carbon (10%) and 2.5 ml of isopropanol were added thereto. Then, air was introduced into the resulting solution at a flow rate of 50 ml/min with stirring at 70° C. While keeping the pH at neutral by adding 1M sodium hydrogen carbonate dropwise, the reaction was carried out for 2.5 hours. After filtration, the filtrate was subjected to ion exchange chromatography (Dowex I) to yield 10.5 g of carboxyl-$\beta$-CD.

Elementary analysis: $C_{24}H_{71}O_{36}N$, MW 1165 ($NH_4$ salt)

|  | C (%) | H (%) | O (%) | N (%) |
| --- | --- | --- | --- | --- |
| Calcd. | 43.25 | 6.14 | 49.41 | 1.20 |
| Found | 43.30 | 6.16 | 49.40 | 1.14 |

(2) Synthesis of carboxyl-G5P

In 1 liter of 10 mM ammonium acetate buffer (pH 6.5), 10 g of carboxyl-$\beta$-CD and 10 g of phenyl $\alpha$-glucoside were dissolved, and 1000 kU of CGTase was added thereto and reacted at 37° C. for 1 hour. Then, the pH was made 4.0 with acetic acid, and 20 kU of glucoamylase was, added thereto and the reaction was carried out at 37° C. for 10 hours. After freeze-drying the reaction solution, purification was carried out by using a column (30×2400 mm) packed with Bio-Gel p-2 (mfd. by Bio-Rad Co.) equilibrated with 20 mM acetic acid to give 1.2 g of carboxyl-G5P.

The number of glucose residue per phenyl group in the resulting carboxyl-G5P was analyzed by gas-liquid chromatography (GLC) as follows.

G.L.C. analyses

Glucose residue and carboxyl glucose residue in carboxyl G5P were analyzed by G.L.C. (column, 2% OV-17 on Chromosorb W. (mfd. by Wako Pure Chemical Industries, Ltd., 0.4×200 cm) after methanolysis (1.4M HCl-methanol, 90° C. for 2 hours) followed by trimethylsilylation with hexamethyldisilazane and trimethylsilyl chloride in pyridine. The temperature was programmed from 110 to 250° C. at the rate of 4° C. increments per minute. The concentration of phenyl group was taken as unity, and the content was estimated from the absorbance at 265 nm in 0.1M acetic acid solution. Further, the phenyl group was measured quantitatively from the absorbance at 265 nm in 0.1M acetic acid. As a result, the ratio of glucose/phenol in the carboxyl-G5P was 3.9.

From the above results and the fact that the carboxyl-G5p was not acted by glucoapylase, the structure of carboxyl-G5P was estimated as follows:

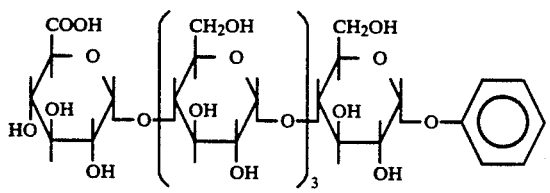

The mass spectrum of this compound is shown in FIG. 1.

Example 4

Synthesis of O-6-deoxy-6-[(2-pyridyl)amino]-α-D-glucopyranosyl-(1→4)-O-α-D-glucopyranosyl-(1→4)-O-α-D-glucopyranosyl-(1→4)-O-α-D-glucopyranosyl-(1→4)-D-glucitol (hereinafter referred to as "FG6R")

In 1 liter of 10 mM ammonium acetate buffer (pH 6.5), 10 g of F-β-CD obtained in the same manner as described in Example 1 (1), and 50 g of maltotriitol were dissolved, and 1000 kU of CGTase was added thereto. The reaction was carried out at 37° C. for 5 hours. After the pH was made 4.0 with acetic acid, 20 kU of glucoamylase was added to the reaction solution and the reaction was carried out at 37° C. for 10 hours. After freezedrying the reaction solution, purification was carried out by using a column (30×1500 mm) packed with Bio-Gel. p-2 (mfd. by Bio-Rad Co.) equilibrated with 50 mM acetic acid to give 1.2 g of FG6R.

EXAMPLE 5

Synthesis of phenyl O-(6-amino-6-deoxy)-α-D-gluco-pyranosyl-(1→4)-O-α-D-glycopyranosyl-(1→4)-O-α-D-glycopyranozyl-(1→4)-O-α-D-glucopyranosyl-(1→4)-α-D-glucopyranoside (hereinafter referred to as "amino-G5P")

(1) Synthesis of mono-6-O-p-toluenesulfonyl β-cyclodextrin

In 100 ml of pyridine, 5.0 g of β-cyclodextrin was dissolved and 0.8 g of p-toluenesulfonyl chloride was added thereto, followed by stirring at 4° C. for 15 hours. After concentration under reduced pressure, the reaction solution was charged in a column (5×60 cm) packed with activated carbon and eluted with water, 30% ethanol, 25% n-propanol, each in amounts of 3 liters. The 25% n-propanol fractions were collected and concentrated under reduced pressure to yield 0.7 g of 6-0-p-toluenesulfonyl β-cyclodextrin.

(2) Synthesis of mono-6-azide-6-deoxy-β-cyclodextrin

In 80 ml of water, 1.0 g of 6-O-p-toluenesulfonyl β-cyclodextrin was dissolved and 1 g of sodium azide was added thereto. The reaction was carried out at 95° C. for 90 minutes. After the reaction, the reaction solution was concentrated under reduced pressure and separated and purified by gel filtration (Bio-Gel p-2) to yield 0.7 g of mono-6-azide-6-deoxy-β-cyclodextrin.

(3) Synthesis of amino-G5P

In 50 ml of 10 mM ammonium acetate buffer (pH 6.5), 0.5 g of mono-6-azide-6-deoxy-β-cyclodextrin and 0.5 g of phenyl α-D-glucopyranoside were dissolved and 50 kU of CGTase was added thereto. The reaction was carried out at 37° C. for 2 hours. After the pH was made 4.0 with acetic acid, 1 kU of glucoamylase was added to the reaction solution, followed by reaction at 37° C. for 10 hours. To the reaction solution, 0.1 g of 10% palladium-carbon was added and hydrogen gas was flowed into the reaction solution at 25° C. for 8 hours with stirring. After freeze-drying the reaction solution, the reaction solution was separated and purified by gel filtration (Bio-Gel p-2) to give 80 mg of amino-G5P.

The number of glucose residue per phenyl group in the amino-G5P was measured by gas-liquid chromatography in the same manner as described in Example 3. As a result, the ratio of glucose/phenol in amino-G5P was 3.6.

From the results mentioned above and the fact that the amino-G5P was not acted by glucoamylase and the color development by ninhydrin was observed on a TLC plate, the structure of amino-G5P was estimated as follows:

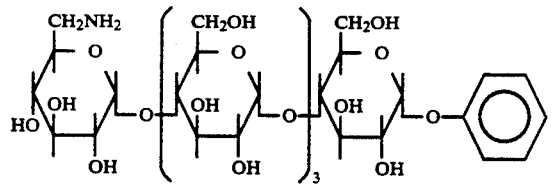

Figure 2:
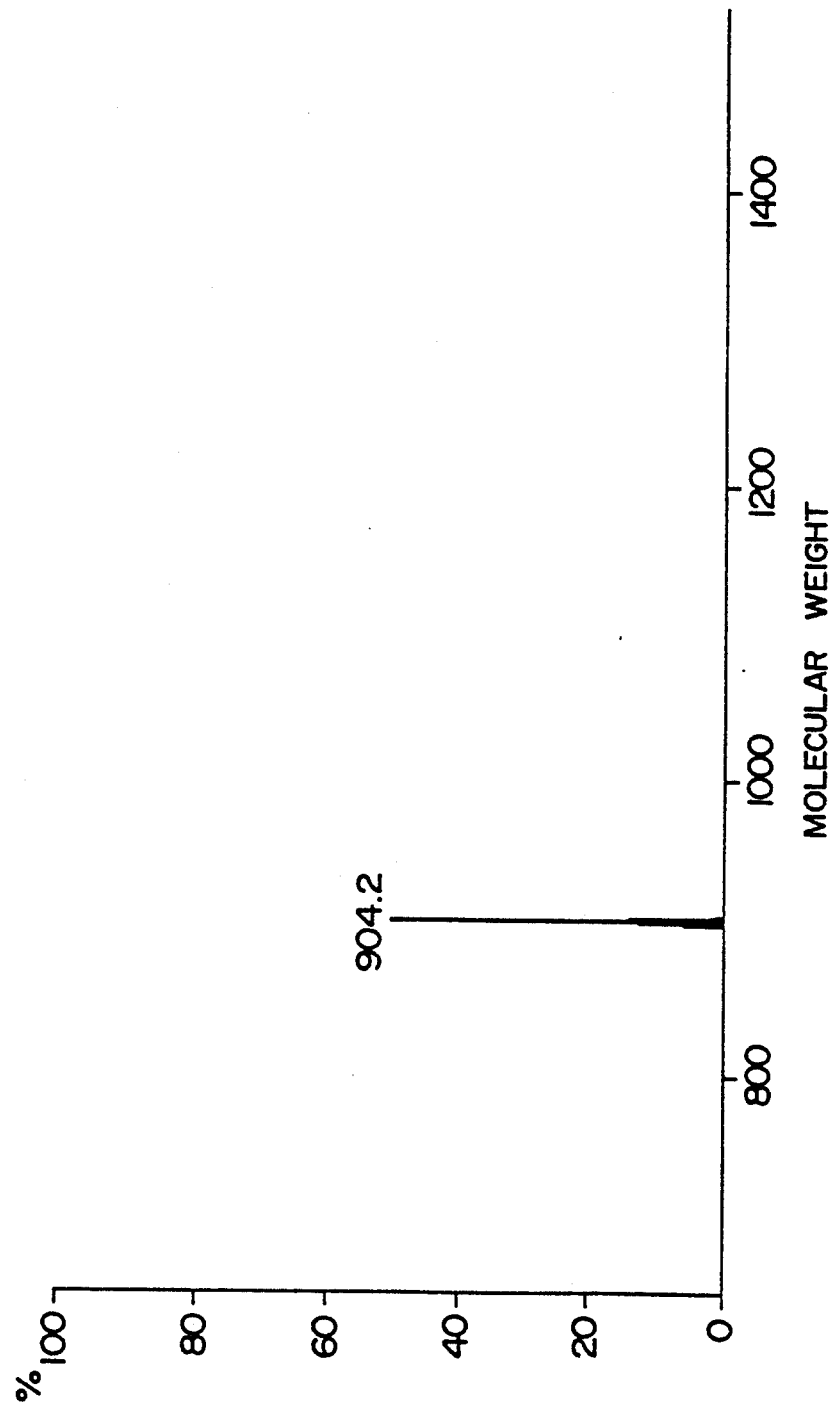

The mass spectrum of this compound is shown in FIG. 2.

EXAMPLE 6

Synthesis of p-nitrophenyl O-(6-O-benzyl)-α-D-glycopyranosyl-(1→4)-O-α-D-glucopyranosyl-(1→4)-O-α-D-glucopyranosyl-(1→4)-O-α-D-glucopyranosyl-(1→4)-α-D-glucopyranoside (hereinafter referred to as "BG5P")

(1) Synthesis of mono-o-benzyl-β-cyclodextrin (hereinafter referred to as "benzyl-β-CD")

In 120 ml of water, 15 g of β-cyclodextrin and 13.5 g of sodium hydroxide were dissolved, and 15 ml of benzyl chloride was added thereto. The reaction was carried out at 10° C. for 2 hours with stirring. After the reaction, the pH was made 7.0 with 6N HCl and 1 liter of acetone was added thereto. The deposited precipitate was filtered and 5 g of benzyl-β-CD was obtained (a mixture of substituted bodies having substituents at $C_2$, $C_3$, and $C_6$ positions).

(2) Synthesis of BG5P

In 1 liter of 10 mM ammonium acetate buffer (pH 6.5), 10 g of benzyl-β-CD and 10 g of p-nitrophenyl α-D-glucopyranoside were dissolved and 1000 kU of CGTase was added thereto. The reaction was carried out at 37° C. for 5 hours with stirring. After making the pH 4.0 with acetic acid, 20 kU of glucoamylase was added thereto and the reaction was carried out at 37° C. for 10 hours. After freeze-drying the reaction solution, purification was carried out by using a column (30×1500 mm) packed with Bio-Gel P-2 (mfd. by Bio-Rad Co.) equilibrated with 50 mM acetic acid to give 1.6 g of crude BG5P (a mixture of compounds having substituents at $C_2$, $C_3$, and $C_6$ positions). This was separated and purified by high performance liquid chromatography (HPLC) to give 180 mg of $C_6$ position substituted body (700 mg of $C_2$ position substituted body and 650 mg of $C_3$ position substituted body).

HPLC: content 96% [column: silica gel Z-ODS, $5C_{18}$ (a trade name, mfd. by Wako Pure Chemical Industries, Ltd., 10×300 mm); eluate: linear gradient of 10% $CH_3CN$ - 0.1% AcOH and 90% $CH_3CN$ - 0.1% AcOH, flow rate 3 ml/min, measured at 305 nm]

Figure 3:
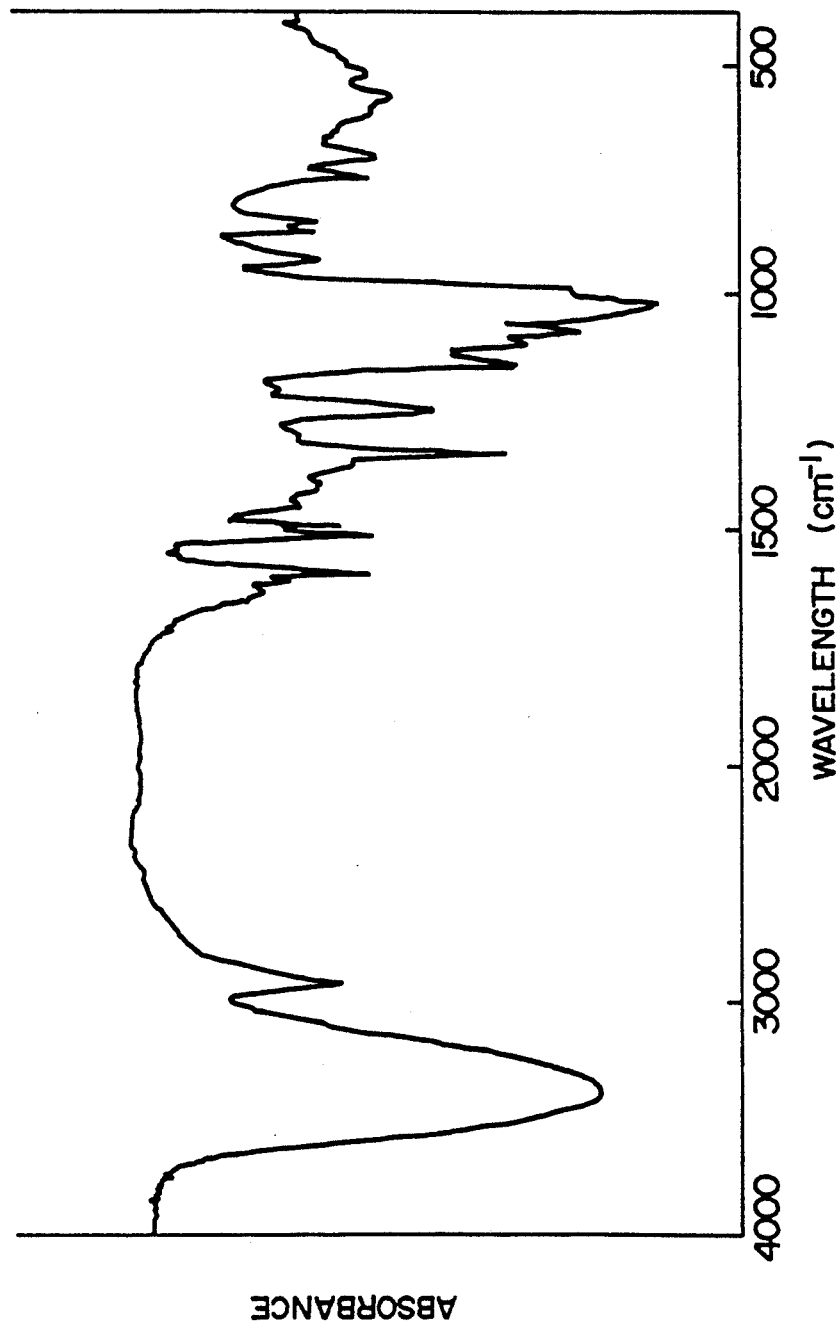
FIG. 3 is an IR chart of the oligosaccharide obtained in Example 6.

IR: as shown in FIG. 3.

Figure 4:
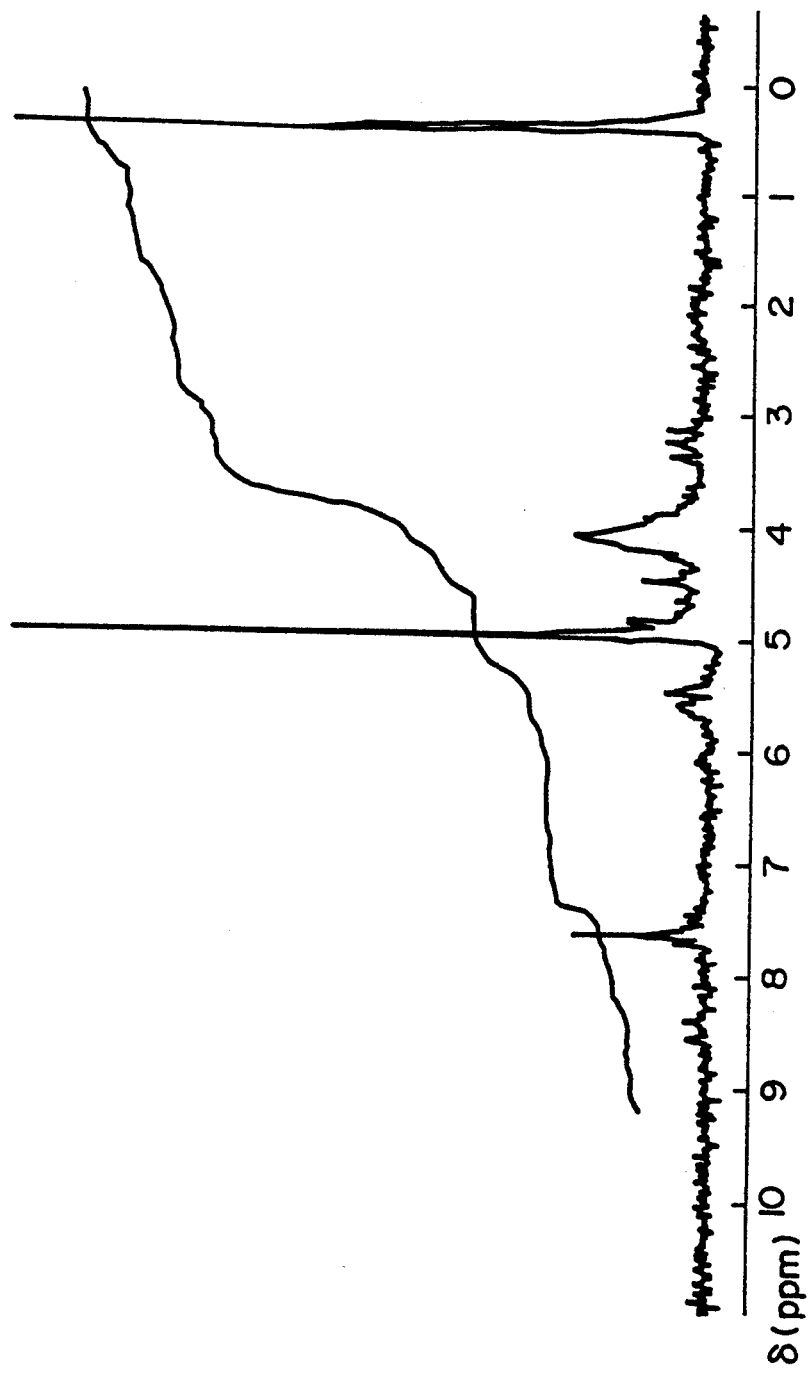
FIGS. 4 and 5 are 'H-NMR charts of the oligosaccharides obtained in Examples 6 and 8, respectively.

$^1$H-NMR: as shown in FIG. 4.

G.L.C. analyses ... Glucose residue and benzyl glucose residue in BG5P were analyzed by G.L.C. (column, 2% OV-17 on chromosorb mfd. by Wako Pure Chem. Ind. Ltd., 0.4×200 cm) after methanolysis (1.4M HCl-methanol, 90° C. for 2h) followed by trimethylsilylation with hexamethyldisilazane and trimethylsilyl chloride in pyridine. The temperature was programmed from 110 to 250° C. at the rate of 4° C. increments per minute. The concentration of p-nitrophenyl group was taken as unity, and the content was estimated from the absorbance at 305 nm in 0.1M acetic acid solution.

From the results mentioned above and the fact that BG5P was not acted by glucoamylase, the structure of BG5p was estimated as follows:

EXAMPLE 7

Synthesis of p-nitrophenyl O-(6-α-methyl)-α-D-glycopyranosyl-(1→4)-O-α-D-glucopyranosyl-(1→4)-O-α-D-glucopyranosyl-(1→4)-O-α-D-glucopyranosyl-(1→4)-α-D-glucopyranoside (hereinafter referred to as "MG5P")

(1) Synthesis of mono-α-methyl-β-cyclodextrin (hereinafter referred to as "methyl-β-CD")

In 120 ml of water, 10 g of β-cyclodextrin and 13.5 g of sodium hydroxide were dissolved and 2.7 g of dimethyl sulfate was added thereto. The reaction was carried out at 10° C. for 2 hours. After the reaction, the pH was made 7.0 with 6N HCl, and 1 liter of acetone was added to the reaction solution. The deposited precipitate was filtered to give 2 g of methyl-β-CD.

(2) Synthesis of MG5P

In 1 liter of 10 mM ammonium acetate buffer (pH 6.5), 10 g of methyl-β-CD and 10 g of p-nitrophenyl α-D-glucopyranoside were dissolved and 1000 kU of CGTase was added thereto. The reaction was carried out at 37° C. for 5 hours with stirring. After making the pH 4.0 with acetic acid, 20 kU of glucoamylase was added to the reaction solution and the reaction was carried out at 37° C. for 10 hours. After freeze-drying the reaction solution, purification was carried out by using a column (30×1500 mm) packed with Bio-Gel P-2 (mfd. by Bio-Rad Co.) equilibrated with 50 mM acetic acid to give 1.5 g of crude MG5P (a mixture of compounds having substituents at $C_2$, $C_3$, and $C_6$ positions). This was separated and purified by reverse high performance liquid chromatography (HPLC) to give 160 mg of $C_6$ position substituted body (680 mg of $C_2$ position substituted body and 560 mg of $C_3$ position substituted body).

HPLC: content 93% (measuring conditions were the same as described in Example 6).

The ratio of glucose/p-nitrophenol of MG5P obtained in the same manner as described in Example 6 was 3.9.

From the results mentioned above and the fact that MG5P was not acted by glucoamylase, the structure of MG5P was estimated as follows:

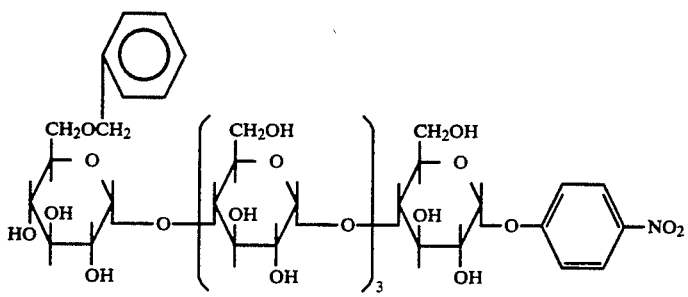

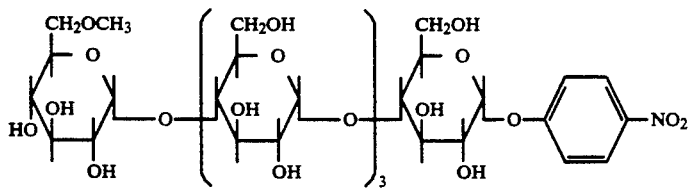

EXAMPLE 8

Synthesis of p-nitrophenyl O-(6-bromo-6-deoxy)-α-D-glycopyranosyl-(1→4)-O-α-D-glucopyranosyl-(1→4)-O-α-D-glucopyranosyl-(1→4)-α-D-glucopyranoside (hereinafter referred to as "BrG5P")

(1) Synthesis of mono-6-bromo-6-deoxy-β-cyclodextrin (hereinafter referred to as "Br-β-CD")

In 250 ml of DMF, 5 g of mono-6-O-p-toluenesulfonyl β-cyclodextrin synthesized according to the process of Example 5(1) was dissolved and 15 g of lithium bromide was added thereto. The reaction was carried out for 2 hours with refluxing. After concentrating under reduced pressure, 500 ml of acetone was added thereto to deposite a precipitate, which was filtered to give 2.3 g of mono-6-bromo-6-deoxy-β-cyclodextrin.

(2) Synthesis of BrG5P

In 100 ml of 10 mM ammonium acetate buffer (pH 6.5), 1 g of Br-β-CD and 1 g of p-nitrophenyl α-D-glucopyranoside were dissolved and 100 kU of CGTase was added thereto. The reaction was carried out at 37° C. for 5 hours with stirring. After making the pH 4.0 with acetic acid, 2000 U of glucoamylase was added thereto and the reaction was carried out at 37° C. for 10 hours with stirring. The reaction solution was concentrated and purified by a column (30×1500 mm) packed with Bio-Gel P-2 (mfd. by Bio-Rad Co.) equilibrated with 50mM acetic acid to give 0.16 g of BrG5P.

HPLC: content 97% (measuring conditions were the same as described in Example 6)

Figure 5:
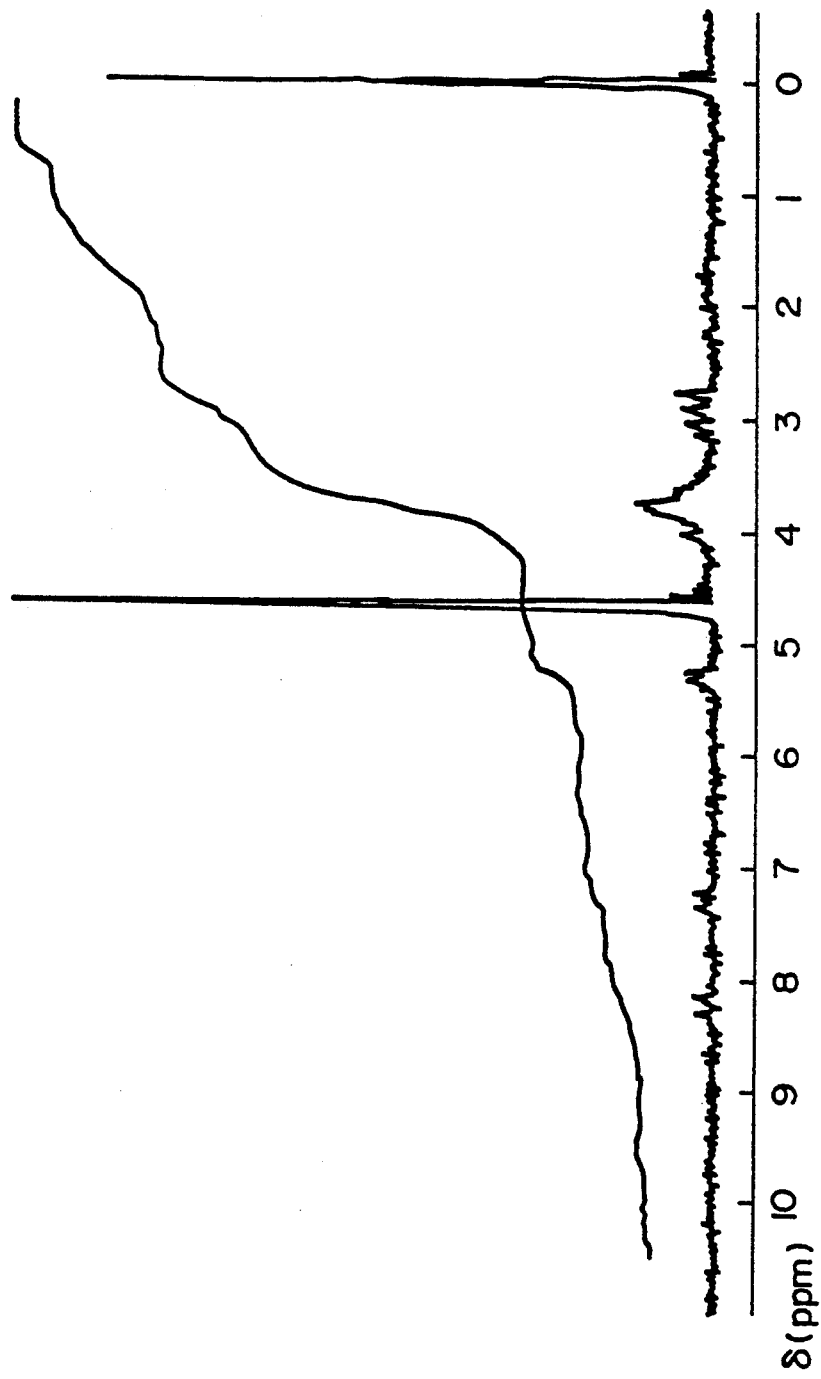

$^1$H-NMR: as shown in FIG. 5.

The ratio of glucose/p-nitrophenol of BrG5P obtained in the same manner as described in Example 6 was 3.6.

From the results mentioned above and the fact that BrG5P was not acted by glucoamylase, the structure of BrG5P was estimated as follows:

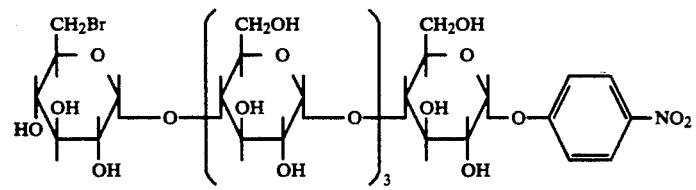

EXAMPLE 9

Synthesis of BG5P

After dissolving 3 g of p-nitrophenyl-α-D-maltopentaoside in 50 ml of DMF, 15 ml of benzaldehyde dimethylacetal and 1 g of p-toluenesulfonic acid (anhydride) were added thereto. The reaction was carried out at 50° C. for 3 hours with stirring. After the reaction, 100 ml of pyridine was added thereto, and 60 ml of benzoyl chloride was added dropwise to carry out the reaction. The reaction solution was poured into a solution of saturated sodium hydrogen carbonate to stop the reaction. The reaction solution was extracted with 200 ml of chloroform and washed with saturated saline solution twice, and the solvent was removed in vacuo. The resulting syrup was transferred to a 1-liter four-necked flask and dissolved in 250 ml of THF, followed by addition and dissolution of 3 g of dimethylamine borane. To this solution, 10 ml of a solution of 0.5M HCl (gas) in diethyl ether was added dropwise with stirring, and the reaction solution was poured into 200 ml of saturated sodium hydrogen carbonate to stop the reaction, followed by extraction with 200 ml of chloroform. After washing twice with saturated saline solution, the solvent was removed in vacuo. To the resulting solution, 500 ml of methanol solution containing 0.1N sodium methoxide was added and stirred at 25° C. for 4 hours, followed by addition of acetic acid for neutralization. After removing the solvent in vacuo, 20 ml of 50 mM acetic acid solution was added and applied to a Bio-Gel p-2 column (mfd. by Bio-Rad Co., 2 cm in diameter×150 cm) equilibrated with 50 mM acetic acid and the BG5P fractions were collected and freeze-dried.

Yield: 450 mg
IR chart: as shown in FIG. 3
$^1$H-NMR: as shown in FIG. 4
HPLC: content 95% (measuring conditions were the same as described in Example 6)
GC composition analysis: glucose/6-O-benzyl-glucose/p-nitrophenyl group=3.8/0.9/1.0 (measuring conditions were the same as described in Example 6)

EXAMPLE 10

Synthesis of p-nitrophenyl O-(6-O-benzyl)-α-D-glycopyranosyl-(1→4)-O-α-D-glucopyranosyl-(1→4)-O-α-D-glucopyranosyl-(1→4)-O-α-D-glucopyranosyl-(1→4)-α-D-glucopyranoside (hereinafter referred to as "BG6P")

After dissolving 3 g of p-nitrophenyl α-D-maltohexaoside in 50 ml of DMF, 15 ml of benzaldehyde dimethylacetal and 1 g of p-toluenesulfonic acid (anhydride) were added thereto and reacted at 50° C. for 3 hours with stirring. After the reaction, 100 ml of pyridine was added thereto and the reaction was carried out while adding 80 ml of benzoyl chloride dropwise with ice cooling. The reaction solution was poured into 300 ml of saturated solution of sodium hydrogen carbonate to stop the reaction. After extracting with 200 ml of chloroform and washing with saturated saline solution twice, the solvent was removed in vacuo. The resulting syrup was transferred to a 1-liter four-necked flask and dissolved in 250 ml of THF, followed by addition and dissolution of 3 g of dimethylamine borane. To this solution, 10 ml of a 0.5M HCl (gas) in diethyl ether was added dropwise with stirring. The reaction solution was poured into 300 ml of a solution of saturated sodium hydrogen carbonate to stop the reaction, followed by extraction with 200 ml of chloroform. After washing with saturated saline solution twice and removing the solvent in vacuo, 500 ml of a methanol solution containing 0.1N sodium methoxide was added thereto, followed by stirring at 25° C. for 4 hours. Then, acetic acid was added for neutralization. After removing the solvent in vacuo, 20 ml of 50 mM acetic acid solution was added thereto and applied to a Bio Gel P-2 column (mfd. by Bio-Rad Co., 2 cm in diameter × 150 cm) equilibrated with 50 mM acetic acid solution The BG6P fractions were collected and freeze-dried.

Yield: 500 mg

HPLC: content 94% (measuring conditions were the same as Example 6)

GC composition analysis: glucose/6-O-benzyl-glucose/p-nitrophenyl group =4.9/0.9/1.0 (measuring conditions were the same as described in Example 6)

EXAMPLE 11

Synthesis of MG5P

After dissolving 5 g of p-nitrophenyl α-D-maltopentaoside in 40 ml of DMF, 50 ml of methylal and 1 g of p-toluenesulfonic acid (anhydride) were added and reacted at 50° C. for 3 hours. After concentrating the reaction solution in vacuo, 300 ml of pyridine and 100 ml of acetic anhydride were added and reacted at room temperature for 12 hours. Then, 500 ml of a solution of saturated sodium hydrogen carbonate was added to the reaction solution to stop the reaction. After extracting by adding 100 ml of chloroform, washing with saturated saline solution was conducted twice, followed by removal of the solvent by distillation. The resulting syrup was transferred to a 1-liter four-necked flask and dissolved in 250 ml of THF, followed by addition and dissolution of 3 g of dimethylamine borane. To this solution, 10 ml of a 0.5M HCl (gas) in diethyl ether was added dropwise with stirring. The resulting syrup was transferred to a 1-liter four-necked flask and dissolved in 250 ml of THF, followed by addition and dissolution of 3 g of dimethylamine borane. To this solution, 10 ml of a 0.5M HCl (gas) in diethyl ether was added dropwise with stirring. To this, 700 ml of methanol solution containing 0.1N sodium methoxide was added and reacted at 25° C. for 4 hours. Then, acetic acid was added for neutralization. After removing the solvent in vacuo, the resulting solution was applied to a Bio-Gel P-2 column (mfd. by Bio-Rad Co., 2 cm in diameter × 150 cm) equilibrated with 50 mM acetic acid. The MG5P fractions were collected and freeze-dried.

Yield: 730 mg

HPLC: content 93% (measuring conditions were the same as Example 6)

EXAMPLE 12

Measurement of α-amylase activity Measuring reagent

A measuring reagent solution was prepared by dissolving 30 mg of BG5P obtained in Example 6 in 30 ml of 50 mmol/1 2-(N-morpholino)ethanesulfonic acid (MES)-NaOH buffer (pH 6.9) containing 400 units of glucoamylase, 300 units of α-glucosidase and 20 mmol/1 of calcium chloride.

Measuring procedure

To 2 ml of the measuring solution 100 μl of a sample serum was added and incubated at 37° C. The change of absorbance of the reaction solution at a wavelength of 405 nm was measured.

Figure 6:
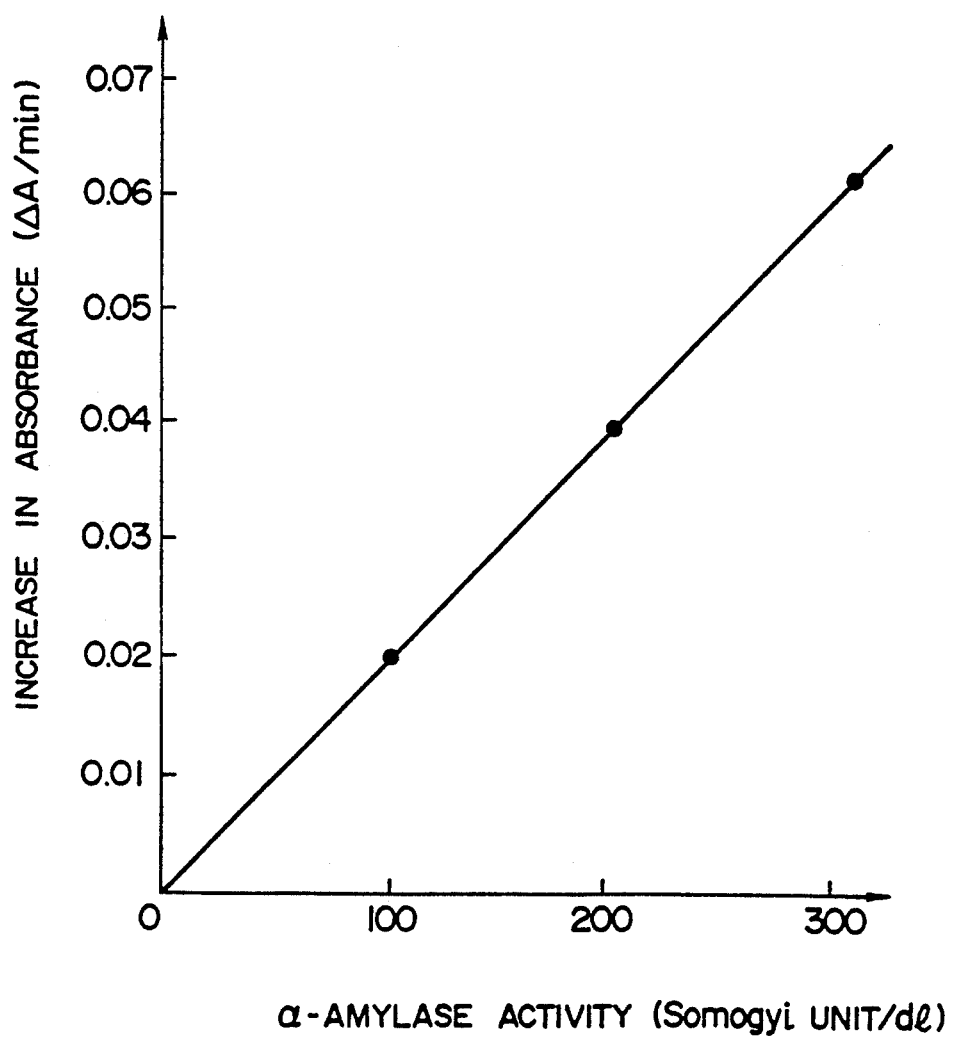
FIGS. 6 and 7 are calibration curves obtained in Examples 12 and 14, respectively.

On the other hand, using a standard sample containing known activities of α-amylase, the calibration curve was prepared in the same manner as mentioned above. From this calibration curve, α-amylase activity of a sample serum was obtained. FIG. 6 shows a relationship between the α-amylase activity at individual diluted stages of a standard sample (Somogyi unit/dl) and the increase in absorbance (ΔA) per minute at a wavelength of 450 nm.

As is clear from FIG. 6, the calibration curve obtained by lining the plots of increased amounts of absorbance (ΔA/min) corresponding to u-amylase activity (Somogyi unit/dl) is linear and passing through the zero point. This means that the calibration curve shows good quantitativeness.

EXAMPLE 13

Measurement of α-amylase activity

Measuring reagent

A measuring reagent solution was prepared by dissolving 2.1 g of N,N-bis(2-hydroxyethyl)-2-aminoethanesulfonic acid, 230 mg of NaCl, 58 mg of $CaCl_2$, 500 mg of NaOH in distilled water, making the total amount 100 ml (pH 7.3) and dissolving 125 mg of BG5P obtained in Example 9 therein.

Solution (A): To 50 ml of the resulting solution, 25,000 units of α-glucosidase was added.

Solution (B): To 20 ml of the solution, 1000 units of glucoamylase was added.

Measuring procedure

To 2 ml of the reagent solution (A) or (B), 50 μl of serum sample was added and incubated at 37° C. The change of absorbance of the reaction solution at a wavelength of 405 nm was measured.

Increasing amounts of absorbances (ΔA) per minute when measured by using 5 kinds of human serum at a wavelength of 405 nm were shown in Table 4.

TABLE 4

| Human serum | Reagent solution | |
|---|---|---|
| No. | A | B |
| 1 | 0.0330 | 0.0335 |
| 2 | 0.0291 | 0.0291 |
| 3 | 0.0329 | 0.0330 |
| 4 | 0.0535 | 0.0537 |
| 5 | 0.0886 | 0.0885 |

As is clear from Table 4, the measuring sensitivity is hardly influenced by the addition of glucoamylase.

EXAMPLE 14

Measurement of α-amylase activity Measuring reagent

A measuring reagent solution was prepared by dissolving 30 mg of BrG5P obtained in Example 8 in ml of 50 mmol/1MES-NaOH buffer (pH 6.9) containing units of glucoamylase, 300 units of α-glucosidase and 20 mmol/1 of calcium chloride.

Measuring procedure

To 2 ml of the measuring solution, 100 μl of a serum sample was added and incubated at 37° C. The change of absorbance of the reaction solution at a wavelength of 405 nm was measured.

Figure 7:
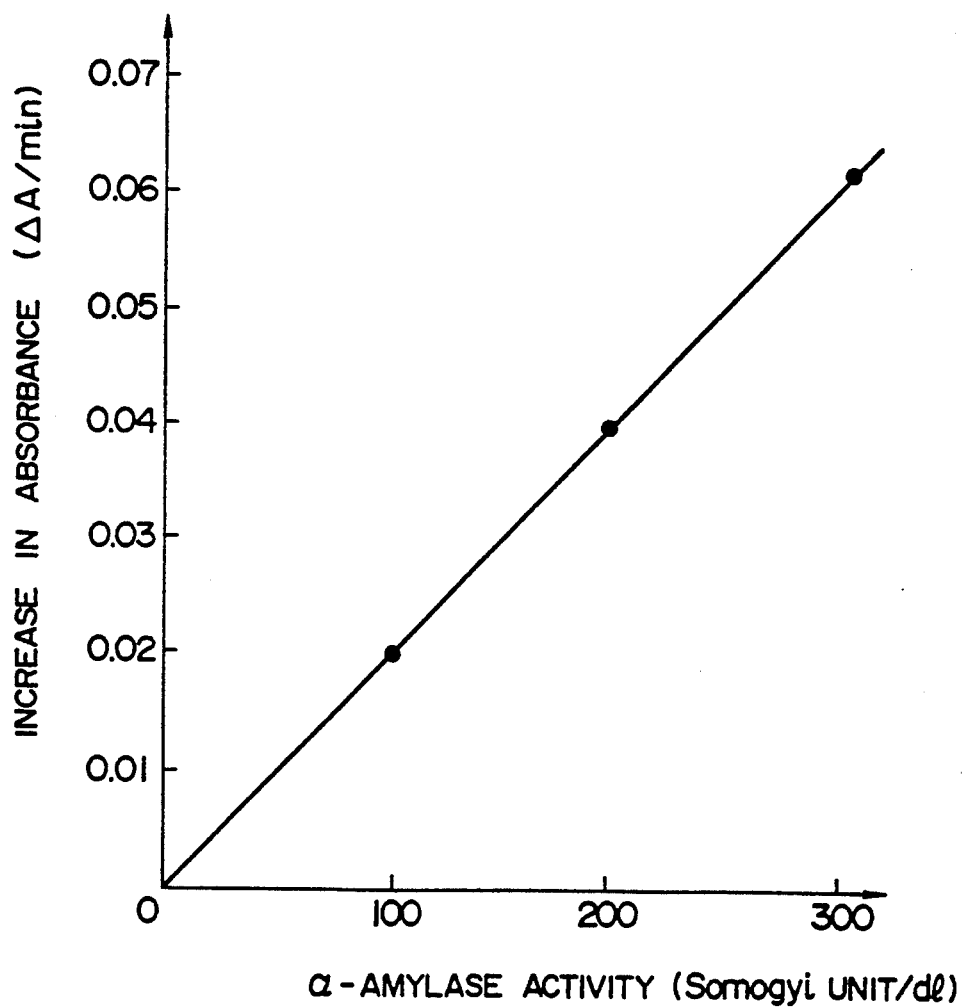

On the other hand, using a standard sample containing known activities of α-amylase, the calibration curve was prepared in the same manner as mentioned above. From this calibration curve, α-amylase activity was obtained. FIG. 7 shows a relationship between the α-amylase activity at individual diluted stages of a standard sample (Somogyi unit/dl) and the increase in absorbance (ΔA) per minute at a wavelength of 405 nm.

As is clear from FIG. 7, the calibration curve obtained by lining the plots of increased amounts of absorbance (ΔA/min) corresponding to α-amylase activity (Somogyi unit/dl) is linear and passing through the zero point. This means that the calibration curve shows good quantitativeness.

What is claimed is:

1. A process for producing a compound of the formula:

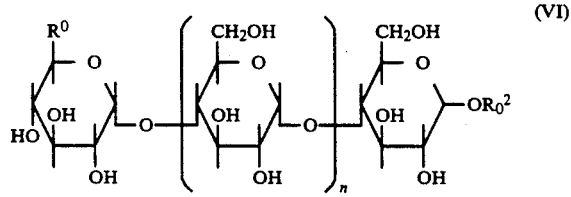

(VI)

wherein $F^0$ is an alkoxymethyl group, a benzyloxymethyl group, an aminomethyl group, a carboxyl group or a halomethyl group; $R^2_0$ is glucitol reside or a group of the formula:

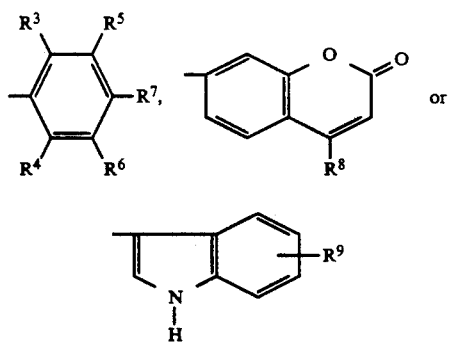

in which $R^3$ through $R^6$ are independently hydrogen, a lower alkyl group, a lower alkoxy group, a nitro group, a carboxyl group, a sulfonic acid group or a halogen atom, and $R^3$ and $R^5$, and/or $R^4$ and $R^6$, may be bonded to form an aromatic ring; $R^7$ is hydrogen, a lower alkoxy group, a halogen atom, or a nitro group; $R^8$ is hydrogen, a methyl group, or a trifluoromethyl group; and $R^9$ is hydrogen or a halogen atom; and n is an integer of 2 to 5, which comprises reacting a modified cyclodextrin with cyclomaltodextrin-glucanotransferase in the presence of an acceptor, and then reacting with glucoamylase or α-glucosidase.

2. A process according to claim 1, wherein the acceptor is glucose, maltose, maltotriose or a derivative thereof.

3. A process for producing a compound of the formula:

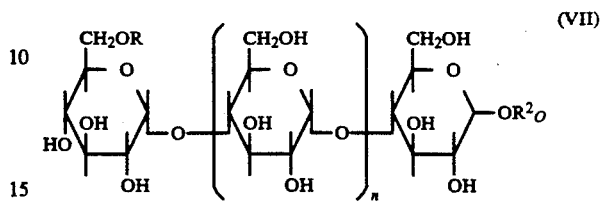

(VII)

wherein R is a benzyl group; a benzyl group substituted with a lower alkyl group having 1 to 4 carbon atoms, a lower alkoxy group having 1 to 4 carbon atoms, an alkyl-substituted amino group, a carboxyl group, a nitro group, or a halogen atom; a 2-, 3- or 4-pyridylmethyl group; a straight- or branched-chain or cyclic alkyl group having 1 to 6 carbon atoms; or an alkenyl group having 1 to 6 carbon atoms; $R^2_0$ is a glucitol residue or a group of the formula:

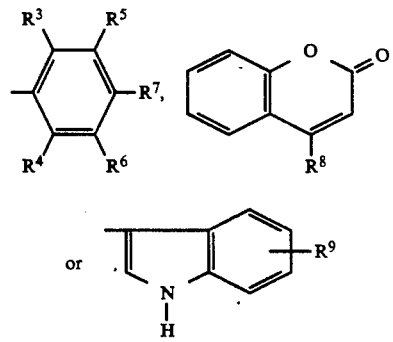

in which $R^3$ through $R^6$ are independently hydrogen, a lower alkyl group, a lower alkoxy group, a nitro group, a carboxyl group, a sulfonic acid group or a halogen atom, and $R^3$ and $R^5$, and/or $R^4$ and $R^6$, may be bonded to form an aromatic ring; $R^7$ is hydrogen, a lower alkoxy group, a halogen atom, or a nitro group; $R^8$ is hydrogen, a methyl group, or a trifluoromethyl group; and $R^9$ is hydrogen or a halogen atom; and n is an integer of 2 to 5, which comprises reacting an oligosaccharide having a substituent which exhibits an optically measurable change upon cleavage at the reducing-end glucose residue with an aldehyde, a ketone, an acetal or a ketal to form 4,6-O-cyclic acetal or 4,6-O-cyclic ketal at the non-reducing-end glucose residue, and reducing said 4,6-O-cyclic acetal or ketal.

4. A process according to claim 3, wherein the oligosaccharide used as a starting material is represented by the formula:

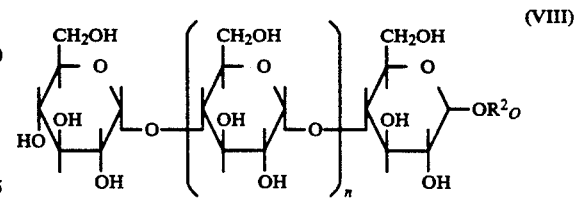

(VIII)

wherein $R^2_0$ and n are as defined in claim 3.

* * * * *